US012807646B2

(12) United States Patent
Zhao et al.

(10) Patent No.: US 12,807,646 B2
(45) Date of Patent: Nov. 24, 2026

(54) MEDICAMENT FOR INHIBITING DIETARY OBESITY AND POLYPEPTIDE USED THEREFOR

(71) Applicant: INSTITUTE OF ZOOLOGY, CHINESE ACADEMY OF SCIENCES, Beijing (CN)

(72) Inventors: Fangqing Zhao, Beijing (CN); Zhanzhan Li, Beijing (CN)

(73) Assignee: INSTITUTE OF ZOOLOGY, CHINESE ACADEMY OF SCIENCES, Beijing (CN)

( * ) Notice: Subject to any disclaimer, the term of this patent is extended or adjusted under 35 U.S.C. 154(b) by 69 days.

(21) Appl. No.: 18/256,201

(22) PCT Filed: Jul. 25, 2022

(86) PCT No.: PCT/CN2022/107650
§ 371 (c)(1),
(2) Date: Jun. 6, 2023

(87) PCT Pub. No.: WO2023/159866
PCT Pub. Date: Aug. 31, 2023

(65) Prior Publication Data

US 2024/0376148 A1 Nov. 14, 2024

(30) Foreign Application Priority Data

Feb. 24, 2022 (CN) ......................... 202210175874.5

(51) Int. Cl.
*C07K 7/06* (2006.01)
*A61K 38/00* (2006.01)
*A61P 3/04* (2006.01)

(52) U.S. Cl.
CPC .................. *C07K 7/06* (2013.01); *A61P 3/04* (2018.01); *A61K 38/00* (2013.01)

(58) Field of Classification Search
CPC ...... C07K 7/06; A61P 3/04; A61P 1/00; A61P 3/06; A61K 38/00
See application file for complete search history.

(56) References Cited

U.S. PATENT DOCUMENTS

2022/0213156 A1* 7/2022 Wehkamp ............... A61P 31/22
2025/0368685 A1* 12/2025 Wehkamp ............... A61P 31/04

FOREIGN PATENT DOCUMENTS

CN 114456232 A 5/2022
WO WO-2020144166 A1 * 7/2020 ............... C07K 7/08
WO WO-2020229349 A1 * 11/2020 ......... C07K 14/4723

OTHER PUBLICATIONS

Tanabe et al., Paneth Cell α-Defensins from Rhesus Macaque Small Intestine. Infect Immun 72 (2004): https://doi.org/10.1128/iai.72.3.1470-1478.2004 (Year: 2004).*

(Continued)

*Primary Examiner* — Randall L Beane
(74) *Attorney, Agent, or Firm* — HAUPTMAN HAM, LLP

(57) ABSTRACT

The present invention provides a polypeptide for inhibiting dietary obesity, the amino acid sequence of which is as follows: $X_1TX_2YX_3$RTGR (SEQ ID NO. 9). The present invention also provides the use of the polypeptide. The polypeptide of the present invention reduces the growth rate of body weight and the deposition of subcutaneous and visceral fat in experimental animals, and can significantly inhibit the occurrence and development of dietary obesity in experimental animals such as mice, rats and rhesus monkeys by reducing appetite. After the polypeptide treatment, the abundance of intestinal symbiotic bacterium *A. muciniphila* in experimental animals is significantly increased.

3 Claims, 4 Drawing Sheets

Specification includes a Sequence Listing.

(56) References Cited

OTHER PUBLICATIONS

Genbank AAW78346.1, defensin alpha 2 [Papio anubis] (Feb. 3, 2005), attached as 1 page pdf; also available at https://www.ncbi.nlm.nih.gov/protein/AAW78346 (last visited Feb. 17, 2026) (Year: 2005).*
GenBank: AAW51368.1, alpha-defensin 4 precursor [Macaca mulatta] (Dec. 21, 2016), attached as 2 page pdf; also available at https://www.ncbi.nlm.nih.gov/protein/AAW51368.1 (last visited Feb. 17, 2026). (Year: 2016).*
International Search Report and Written Opinion issued in International Application No. PCT/CN2022/107650; mailed Oct. 28, 2022; 38 pgs.
Tomas, Eva et al; GLP-1-derived nonapeptide GLP-1(28-36)amide inhibits weight gain and attenuates diabetes and hepatic steatosis in diet-induced obese mice; Regulatory Peptides 169; 2011; pp. 43-48.

* cited by examiner

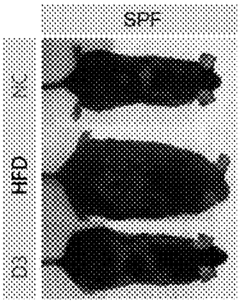
FIG.3
FIG. 4A
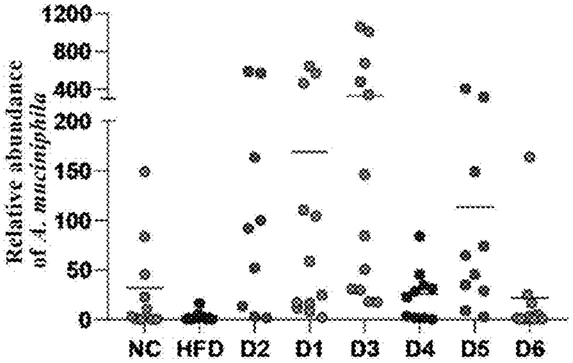
FIG. 4B
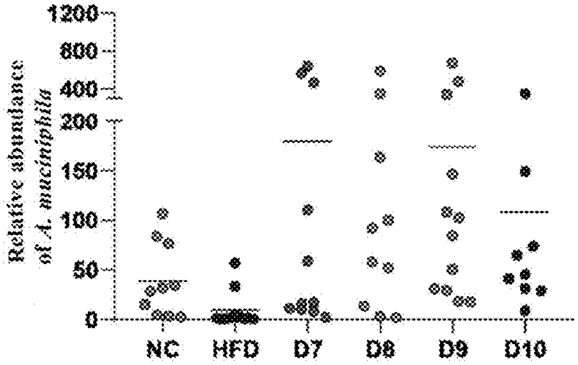
FIG. 5A
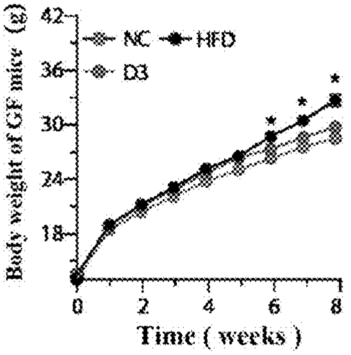
FIG. 5B
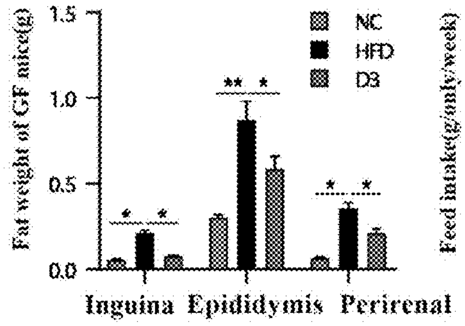
FIG. 5C
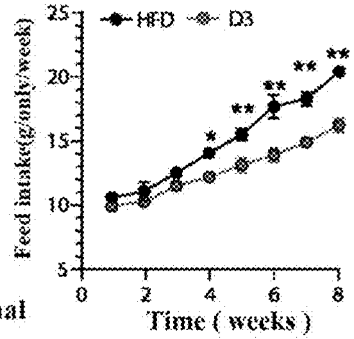

FIG. 6A
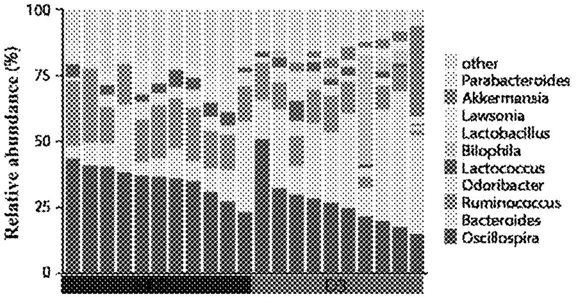
FIG. 6B
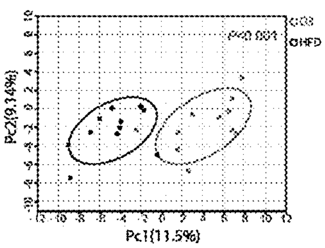
FIG. 6C
FIG. 7A
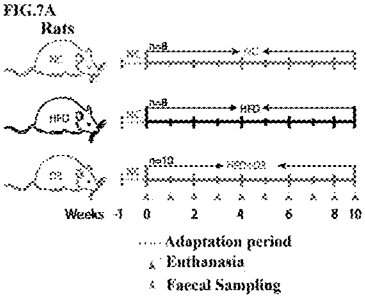
FIG. 7B
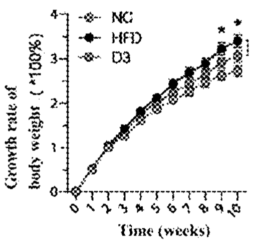
FIG. 7C
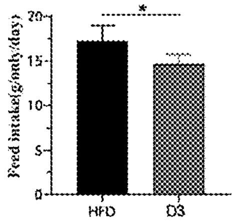
FIG. 7D
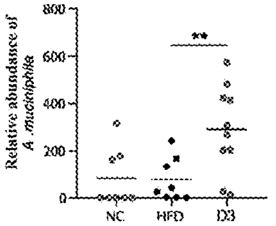
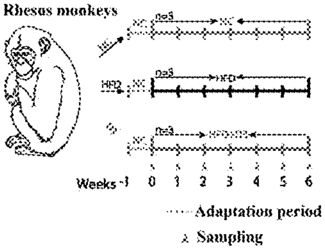
FIG. 7E
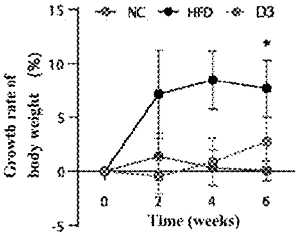
FIG. 7F
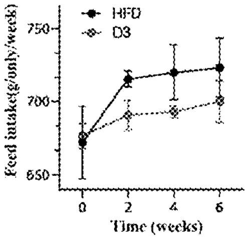
FIG. 7G
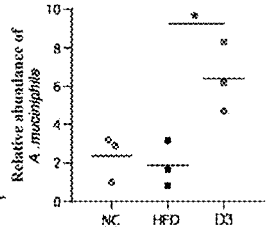
FIG. 7H

MEDICAMENT FOR INHIBITING DIETARY OBESITY AND POLYPEPTIDE USED THEREFOR

RELATED APPLICATIONS

The present application is a U.S. National Phase of International Application Number PCT/CN2022/107650 filed Jul. 25, 2022, and claims priority to Chinese Application Number 202210175874.5 filed Feb. 24, 2022.

INCORPORATION BY REFERENCE

The sequence listing provided in the file entitled C6351-100_SQL-1.xml, which is an Extensible Markup Language (XML) file that was created on Dec. 1, 2025, and which comprises 11,793 bytes, is hereby incorporated by reference in its entirety.

FIELD OF THE INVENTION

The present invention relates to a polypeptide for inhibiting dietary obesity and use thereof in the field of biotechnology.

BACKGROUND OF THE INVENTION

1. Overview of Obesity

Obesity, defined as a body mass index (BMI)>30 kg/m$^2$, has nearly tripled globally since 1975. It is estimated that more than 1.9 billion adults were overweight in 2014, of whom more than 600 million were classified as obese. Obesity is now becoming a global epidemic with a high risk of developing non-communicable diseases including type 2 diabetes (T2D), cardiovascular disease, stroke, cancer and depression. Various strategies have been developed to combat obesity and overweight, mainly by reducing energy intake and increasing metabolic expenditure of these two ways.

2. Weight Loss Medicine that have been Approved by the FDA

Diet and lifestyle measures remain the fundamental focus of patients coping with obesity, but as the disease progresses, patients have to frequently require medical or surgical interventions, which are often limited by weight loss effects, side effects, surgical risks, and obesity recurrence. There is growing interest in pharmacotherapies that support weight loss to reduce obesity and obesity-related complications. The study showed that a 5% weight loss was associated with sustained improvements in key cardiovascular risk factors such as blood pressure and lipid profile. Therefore, many regulatory agencies use 5% total weight loss to determine whether a medicament can cause meaningful weight loss. To date, the U.S. Food and medicine Administration (FDA) has approved six pharmacotherapies to treat obesity(Orlistat, Phentermine/topiramate, Lorcaserin, Naltrexone/bupropion, Liraglutide and semaglutide), which generally support weight loss by enhancing satiety, inhibiting hunger, or increasing fat catabolism.

Orlistat is a selective pancreatic lipase inhibitor, which regulates intestinal digestion and fat absorption, and is suitable for patients with BMI≥30 kg/m$^2$ or ≥28 kg/m$^2$ with other risk factors (such as high blood pressure, diabetes, hyperlipidemia). Although obese patients can lose 2.9-3.4 kg of body weight within 12 months using orlistat, common side effects such as nausea and vomiting, decreased absorption of fat-soluble vitamins, and celiac diarrhea.

Phentermine is a sympathomimetic that inhibits appetite, and topiramate, an anticonvulsant, increases its weight loss effects when combined with phentermine. A meta-analysis found that use of the medicine resulted in an average weight loss of 9.8 kg in randomized controlled trials. Medicine side effects include insomnia, dizziness, and paresthesias.

Lorcaserin is a medicament that inhibits appetite by activating hypothalamic 5-HT2C receptors. With the same scope of application as orlistat, obese subjects during the medication period can additionally lose about 3.2-3.6 kg of weight per year, and metabolic parameters including blood pressure and lipids have also improved.

Naltrexone and bupropion, when combined, promote satiety by enhancing release of MSH (melanocyte-stimulating hormone) mediated by hypothalamic POMC neuron, thereby reducing food intake and increasing energy expenditure. Studies have shown that obese subjects during the medication period lost an additional 4.8% (average 4.4 kg) per year, and side effects included nausea, headache and dizziness.

Liraglutide is a glucagon-like peptide-1 (GLP-1) agonist initially used in the treatment of type 2 diabetes (T2D), which can increase satiety and delay gastric emptying by stimulating the hypothalamus, thereby reducing food intake and resulting in weight loss, compared with placebo, subjects can lose an additional 5.3-5.9 kg per year. Common side effects include nausea/vomiting and pancreatitis. Weight loss costs about $1300/month.

In June 2021, the FDA approved Novo Nordisk's semaglutide as a weight loss medicine. Also as a GLP-1 agonist, the design of semaglutide involves 129 sites in 16 countries on 4 continents, and the results of Phase 3 clinical trials involving 1961 overweight or obese adults showed that patients treated with a subcutaneous dose of 2.4 mg/week lost an average of 15.3 kg (14.9% of initial body weight), which was 12.7 kg (12.4%) more than those randomized to receive placebo, with a mean body mass index (BMI) dropped 5.54. Similar to other GLP-1 receptor agonists, the adverse events of semaglutide mainly occurred in the gastrointestinal tract, and the incidence of gallbladder-related diseases increased. Table 1.1 lists approved pharmacotherapies for weight loss in obese subjects.

3. Weight Loss Medicines that are in Phase III Clinical Trials

GLP-1 has a good effect on hypoglycemia, weight loss and cardiovascular disease prognosis, while insulin-stimulating polypeptide (GIP), one of the incretin hormones, has poor hypoglycemic effect, but there is evidence that, compared with single administration, Co-infusion of GLP-1 and GIP can produce a synergistic effect, leading to a significant increase in insulin response and glucagon suppression response. These observations inspired the researchers to develop a dual GIP/GLP-1 receptor agonist, called a "twin enterin." As a novel dual GIP/GLP-1 receptor agonist, tirzepatide is a 39-amino acid peptide synthesized based on the natural GIP sequence. Preclinical trials and Phase 1 and Phase 2 clinical trials have shown that tizitide has significant hypoglycemic and weight loss effects. After 26 to 40 weeks of treatment, it can lose an additional weight of more than 10 kg compared with placebo. Adverse reactions are comparable to those of GLP-1 receptor agonists. Long-term, large phase 3 clinical trials of tizitide for weight management and cardiovascular prognosis in diabetic patients are ongoing.

4. Obesity and Intestinal Flora

Although there are many causes of human obesity, in recent years, with the research on intestinal microbes in full swing, various studies have fully explained the role of the structure of intestinal flora in human metabolism and energy balance, as well as the adverse effects of microecological disorders on human physiology and health. The human intestinal flora has major health-maintaining functions, including providing the body with essential nutrients, cellulose digestion, vitamin K synthesis, and promoting angiogenesis. The composition of the intestinal flora varies with the host's genotype and dietary category, and its dominant role in the pathogenesis of obesity includes the regulation of inflammatory responses, energy metabolism, and body weight homeostasis. For example, the interaction between bacteria and a fat-rich diet in the small intestine is directly linked to weight gain and obesity, which can lead to inflammatory response and insulin resistance; certain enterobacteria can affect cellular metabolic cycles in intestinal tissues (adipose tissue and liver), and these interactions directly affect lipid and glucose homeostasis.

In addition, the type of diet can directly affect the changes in the host's intestinal flora, and then feed back to the physiological or pathological responses of the host's own intestinal structure. A healthy diet (high in fiber, low in fat, and sugar) is associated with a high diversity of intestinal flora, including a large number of taxa involved in stimulating intestinal mucus production in humans and animals, allowing for an intact mucus layer combined with a tight intestinal epithelium to form a complete intestinal barrier; unhealthy diet (high fat, high sugar, low fiber) is associated with decreased microbial diversity, decreased mucus-stimulating microbes, decreased mucus layer thickness, and increased epithelial leakiness, a process that can lead to a decrease in intestinal barrier function (intestinal leakage) and activation of the intestinal-associated immune system through microbial products such as lipopolysaccharide (LPS).

Dysbacteriosis is associated with many metabolic diseases, especially obesity. The human intestine is densely populated with commensal and symbiotic microbes, mainly bacteria, and about 80%-90% of the bacterial system types are divided into two phyla: Firmicutes (*Clostridium, Enterococcus, Lactobacillus* and Ruminococcus) and Bacteroidetes (*Bacteroides* and *Prevotella*), followed by Actinomycetes (Bifidobacteria) and Proteobacteria (*Pylori* and *Escherichia coli*), the intestinal flora of the healthy adults is mainly composed of Bacteroidetes and Firmicutes. Compared with lean controls, obese patients had a lower relative proportion of *Bacteroides* and a higher proportion of Firmicutes, and the proportion of *Bacteroides* increased significantly after weight loss. Furthermore, compared with normal-weight fetuses among twins, obese fetuses had lower bacterial diversity and a lower proportion of *Bacteroides*, but a higher proportion of Actinobacteria, while the proportion of Firmicutes does not differ significantly. Of course, weight loss also in turn affects the composition of the intestinal flora, which tends to absorb and store energy more efficiently in obese individuals compared to lean individuals, ultimately leading to greater fat storage. Backhed et al. showed that when normal-reared mice were colonized with intestinal flora, germ-free mice showed a significant increase in body fat mass despite reduced food intake. When intestinal flora from obese human or mouse donors were used to perform FMT on normal mice, the increase rate of body fat in the latter was significantly higher than that of the intestinal flora of transplanted lean donors.

5. Regulating the Structure of Intestinal Flora can Improve Obesity

Substantial evidence suggests that the intestinal flora plays an important role in the development of obesity, obesity-related inflammation, and insulin resistance. There are currently many interventions to change the microbial structure, such as probiotics, prebiotics and fecal microbiota transplantation. Identifying the hosts of obesity and the environmental factors involved as soon as possible can help alleviate the worldwide obesity epidemic.

Probiotics are defined as "live microbes that are beneficial to human health" when the dose is large enough. Using probiotics or dietary intervention to regulate or treat obesity by shaping enterobacteria can affect the host's body weight, glucose and fat metabolism, improve insulin sensitivity, and reduce chronic systemic inflammation in humans. The most commonly used probiotics are *Bifidobacterium* and *Lactobacillus*, but their effects on obesity are species and strain specific. Yoo et al. found that probiotic foods containing *L. curvatus* HY7601 could significantly reduce hepatic fat accumulation in diet-related obesity compared with *L. plantarum* KY1032, which significantly inhibited the expression of genes involved in preventing the synthesis of different fatty acid enzymes in the liver. A study of 14 live probiotic strains including *Bifidobacterium, Lactobacillus, Lactococcus* and *Propionibacterium* found that administration of a probiotic blend including concentrated biomass during childhood improved insulin sensitivity and significantly reduced total body weight and visceral adipose tissue weight in children. Intragastric administration of *Bacteroides acidifaciens* to obese mice can stimulate the activation of fat oxidation through the cholic acid TGR5-PPARα axis in adipose tissue, resulting in increased energy consumption and weight loss in mice. Chagwedera et al. reported that selective deficiency of *L. johnsonii* Q1-7 strains could regulate the production of self-specific IgA by activating mTORC1 signaling in CD11c cells, ultimately leading to the reduction of food intake and body weight in Tsc1 f/f CD11c are mice.

In addition, some medicines have been shown to improve the metabolic status of obese patients by improving the microbial structure. For example, the antioxidant tempol can preferentially reduce the activity of lactic acid bacteria and their bile salt hydrolases to change the structure of intestinal flora, thereby causing the accumulation of taurine-3-mouse cholic acid in the intestine, which is involved in the regulation of bile acid, lipid and glucose metabolism, and ultimately reduces obesity in mice. Cranberry extract, miR-30d and metformin can protect mice from diet-induced obesity by increasing *Akkermansia muciniphila* in the intestinal flora. Recent studies have shown that daily administration of *A. muciniphila* can counteract the development of obesity in mice caused by a high-fat diet.

Fecal microbiota transplantation (FMT) is a promising new solution to directly transplant donor bacteria into receptors, but related scientific research is still in its initial stage. A number of studies have confirmed that when obese mice are transplanted to the feces of lean mice, weight loss occurs. On the contrary, according to the study of Elaine et al., FMT capsules from lean donors were given to obese adults for at least 12 weeks. Although bacteria were detected to have been implanted, no significant clinical metabolic effects were observed. The scheme of FMT and symbiotic bacteria intervention is in a stage of vigorous development.

6. Brief Introduction of Polypeptide Medicines

Polypeptides are small molecular compounds composed of amino acids. Generally speaking, peptides consisting of 2-9 amino acids are called oligopeptides, and those longer than 10 amino acids are called polypeptides, which often play an important role at the physiological or pathological level and participate in the occurrence and development of various diseases. Polypeptide can be divided into endogenous polypeptides and exogenous polypeptides according to different sources. Endogenous polypeptides are important biological process regulators derived from endogenous proteolysis or non-coding RNA-encoded peptides, which exist in the human body, including hormones, neurotransmitters, growth factors, ion channel ligands, etc., which can promote energy metabolism, inhibition of insulin resistance and other biological activities. Exogenous polypeptides are biologically active polypeptides that exist in nature, such as plants or animals, and can be divided into physiologically active polypeptides and food protein source polypeptides according to their functions. Physiologically active peptides play an important role in the body, including antimicrobial peptides, neuropeptides and antihypertensive peptides. Food protein source polypeptides include soybean protein hydrolyzate (food additive), aspartic acid methyl ester (sweetener), etc.

The development of polypeptide medicines has become one of the hottest topics in medicine research. The history of peptide medicine discovery began with the use of natural hormones and small peptides with well-studied physiological functions to treat diseases caused by hormone deficiency, for example by injecting insulin or stimulating insulin secretion-related targets such as the GLP-1 receptor to produce insulin to treat diabetes. Finding natural peptide hormones or replacing them with animal homologues, such as insulin, GLP-1, somatostatin, vasopressin, and oxytocin, is an initial strategy for the discovery and development of peptide medicines. With the advent of the new century, peptide medicine development entered a new era, which was significantly accelerated by advances in structural biology, recombinant biologics, and new synthetic and analytical techniques. Some of today's peptide medicines are no longer pure hormone mimics or purely composed of natural amino acids. For example, enfuvirtide, a 36-amino acid biomimetic peptide that mimics human immunodeficiency virus (HIV) proteins, is used in combination therapy for the treatment of HIV-1; ziconotide, a neurotoxic peptide derived from conic snails, is used in the treatment of severe chronic pain; the pharmaceutical industry's research on rare diseases and orphan medicines has also expanded into the field of polypeptides, and examples marketed in this area include teduglutide, a GLP-2 receptor 2 agonist for the treatment of short bowel syndrome; and pasireotide, a somatostatin receptor agonist for the treatment of Cushing's syndrome. Many polypeptide medicines have been used in a wide range of therapeutic areas, such as urology, respiratory, oncology, metabolism, cardiovascular diseases, etc.; GLP-1 analogues are hot in the diabetes and weight loss market. In view of the special pharmacological characteristics and intrinsic properties of peptide medicines, compared with protein-based biopharmaceuticals, polypeptides are an excellent starting point for designing new medicines, and the production of small peptides is not complicated, so the production cost is also lower. This feature makes peptide medicines a better choice between small molecule and large molecule protein medicines. So far, polypeptide medicines account for a large proportion of the pharmaceutical market, with global sales of more than 70 billion US dollars in 2019, more than twice as much as in 2013, and more than 170 polypeptides are in active clinical development.

At present, a variety of peptides to prevent obesity have been developed on the market, such as neuropeptide Y receptor antagonists, glucagon-like peptide-1 (GLP-1), atrial natriuretic peptide and brain natriuretic peptide, Ghrelin11, etc. However, apart from the fact that they are all injectable, the aforementioned peptides are more than 20 amino acids in length and are therefore unlikely to escape protease degradation. However, small molecules also have some disadvantages: accumulation in organs and production of toxic metabolites, etc., which in turn lead to side effects. Therefore, further studies are needed to find or modify more endogenous peptides that are much smaller and lack cumulative toxicity for the treatment of obesity.

SUMMARY OF THE INVENTION

The technical problem to be solved by the present invention is how to prepare a medicament for preventing and/or treating dietary obesity, and/or how to prepare an inhibitor of dietary obesity.

In order to solve the above technical problems, the present invention provides a series of polypeptides or their medicinal salts or their derivatives. The polypeptides can be collectively referred to as HD, which is a 9-peptide, and its amino acid sequence formula is as follows (N-terminal to C-terminal)

HD sequence formula: $X_1TX_2YX_3RTGR$ (SEQ ID NO. 9);

where, the letter T represents threonine (Thr), the letter Y represents tyrosine (Tyr), the letter R represents arginine (Arg), and the letter G represents glycine (Gly); $X_1$ can be one of glycine (Gly, G) and arginine (Arg, R); $X_2$ can be one of arginine (Arg, R) and cysteine (Cys, C); $X_3$ can be one of lysine (Lys, K) and cysteine (Cys, C).

The specific amino acid sequence of HD is any one of the following:

D1: RTRYKRTGR (as shown in SEQ ID NO: 1 in the sequence listing);

D2: GTCYKRTGR (as shown in SEQ ID NO: 2 in the sequence listing);

D3: RTRYCRTGR (as shown in SEQ ID NO: 3 in the sequence listing);

D5: RTCYKRTGR (as shown in SEQ ID NO: 4 in the sequence listing);

D7: GTCYCRTGR (as shown in SEQ ID NO: 5 in the sequence listing);

D8: GTRYKRTGR (as shown in SEQ ID NO: 6 in the sequence listing);

D9: RTCYCRTGR (as shown in SEQ ID NO: 7 in the sequence listing);

D10: GTRYCRTGR (as shown in SEQ ID NO: 8 in the sequence listing).

Preferably, the HD is D3: RTRYCRTGR (as shown in SEQ ID NO: 3 in the sequence listing).

The derivative can be a linker obtained by connecting an amino-terminal protecting group to the amino-terminal of the polypeptide and/or connecting a carboxyl-terminal protecting group to the carboxyl-terminal of the polypeptide. The amino-terminal protecting group can be any group of acetyl, amino, maleyl, succinyl, tert-butoxycarbonyl or benzyloxy or other hydrophobic groups or macromolecular carrier groups; the carboxyl-terminal protecting group can be any group of amino, amide, carboxyl, or tert-butoxycarbonyl or other hydrophobic groups or macromolecular carrier groups.

The present invention also relates to a nucleic acid molecule encoding the above polypeptide or a medicinal salt thereof. The nucleic acid molecule refers to any nucleic acid molecule that encodes the above-mentioned polypeptide or a medicinal salt thereof after translation according to recognized triplet codons.

Among them, the nucleic acid molecule can be DNA, such as cDNA, genomic DNA or recombinant DNA; the nucleic acid molecule can also be RNA, such as mRNA or hnRNA.

The present invention also provides the use of the polypeptide or the medicinal salt or derivative thereof, or the nucleic acid molecule in the preparation of a medicament for preventing and/or treating animal obesity.

The present invention provides the use of the polypeptide or the medicinal salt or derivative thereof, or the nucleic acid molecule in the preparation of an animal obesity inhibitor.

The present invention provides the use of the polypeptide or the medicinal salt or derivative thereof, or the nucleic acid molecule in the preparation of a medicament for inhibiting animal body weight growth.

The present invention provides the use of the polypeptide or the medicinal salt or derivative thereof, or the nucleic acid molecule in the preparation of a medicament for inhibiting subcutaneous and visceral fat deposition in animals.

The present invention provides the use of the polypeptide or the medicinal salt or derivative thereof, or the nucleic acid molecule in the preparation of a medicament for inhibiting animal appetite.

The present invention provides the use of the polypeptide or the medicinal salt or derivative thereof, or the nucleic acid molecule in the preparation of a medicament for adjusting the intestinal symbiotic bacterium of animals.

The present invention provides the use of the polypeptide or the medicinal salt or derivative thereof, or the nucleic acid molecule in the preparation of a medicament for increasing the abundance of the intestinal symbiotic bacterium *Akkermansia muciniphila* of animals.

The above uses all include the step of administering the polypeptide or the medicinal salt or derivative thereof, or the nucleic acid molecule to the subject animal.

In the above uses, the animals are mammals, which can be rodents (such as mice, rats, etc.), primates (such as macaques, humans, etc.), etc.

In the above uses, the obesity can be dietary obesity.

In the above uses, the medicine or the inhibitor can only be the above polypeptide, or can also contain a carrier or excipient.

The carrier material here includes but are not limited to water-soluble carrier materials (such as polyethylene glycol, polyvinylpyrrolidone, organic acids, etc.), insoluble carrier materials (such as ethyl cellulose, cholesterol stearate, etc.), enteric carrier materials (such as cellulose acetate phthalate and carboxymethyl ethyl cellulose, etc.). Specific among these are water-soluble carrier materials. These materials can be used to make a variety of dosage forms, including but not limited to tablets, capsules, drop pills, aerosols, pills, powders, solutions, suspensions, emulsions, granules, liposomes, transdermal agents, buccal tablets, suppositories, freeze-dried powder injections, etc. It can be common preparations, sustained-release preparations, controlled-release preparations and various microparticle medicine delivery systems. In order to make the unit dosage form into tablets, a wide range of carriers known in the art can be used. Examples of carriers are, for example, diluents and absorbents such as starch, dextrin, calcium sulfate, lactose, mannitol, sucrose, sodium chloride, glucose, urea, calcium carbonate, kaolin, microcrystalline cellulose, aluminium silicate, etc.; wetting agents and binders, such as water, glycerin, polyethylene glycol, ethanol, propanol, starch paste, dextrin, syrup, honey, glucose solution, acacia mucilage, gelatin mucilage, sodium carboxymethylcellulose, shellac, methylcellulose, potassium phosphate, polyvinylpyrrolidone, etc.; disintegrants, such as dry starch, alginate, agar powder, brown algae starch, sodium bicarbonate and citric acid, calcium carbonate, polyoxyethylene, sorbitol fatty acid esters, sodium dodecyl sulfonate, methylcellulose, ethyl cellulose, etc.; disintegration inhibitors, such as sucrose, tristearin, cocoa butter, hydrogenated oils, etc.; absorption enhancers, such as quaternary ammonium salts, sodium lauryl sulfate, etc.; lubricants, such as talc, silicon dioxide, corn starch, stearate, boric acid, liquid paraffin, polyethylene glycol, etc. Tablets can also be further made into coated tablets, such as sugar-coated tablets, film-coated tablets, enteric-coated tablets, or double-layer tablets and multi-layer tablets. In order to make the unit dosage form into pills, a wide range of carriers known in the art can be used. Examples of carriers are, for example, diluents and absorbents such as glucose, lactose, starch, cocoa butter, hydrogenated vegetable oils, polyvinylpyrrolidone, Gelucire, kaolin, talc, etc.; binders such as acacia, tragacanth, gelatin, ethanol, honey, liquid sugar, rice paste or batter, etc.; disintegrants, such as agar powder, dry starch, alginate, sodium dodecyl sulfonate, methylcellulose, ethyl cellulose, etc. In order to make the unit dosage form into suppositories, a wide range of carriers known in the art can be used. Examples of carriers are, for example, polyethylene glycol, lecithin, cocoa butter, higher alcohols, esters of higher alcohols, gelatin, semi-synthetic glycerides and the like. In order to make unit dosage form into injection preparations, such as solutions, emulsions, freeze-dried powder injections and suspensions, all diluents commonly used in this field can be used, for example, water, ethanol, polyethylene glycol, 1, 3-propanediol, ethoxylated isostearyl alcohol, polyoxylated isostearyl alcohol, polyoxyethylene sorbitan fatty acid ester, and the like. In addition, in order to prepare isotonic injection, an appropriate amount of sodium chloride, glucose or glycerin can be added to the injection preparations, and in addition, conventional solubilizers, buffers, pH regulators, etc. can also be added. In addition, if necessary, colorants, preservatives, fragrances, correctives, sweeteners or other materials can also be added to the medicinal preparations.

The medicinal salt of the present invention includes acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, D-camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, 8-teoclate salt, iodide, tosylate, triethiodide, lactate, valerate, etc. Depending on the use, medicinal salts can be composed of cations such as sodium, potassium, aluminum, calcium, lithium, magnesium and zinc, bismuth, etc. It can also be formed by bases such as ammonia, ethylenediamine, N-methyl-glutamine, lysine, arginine, ornithine, choline, N,N'-dibenzylethylene-diamine, chloroprocaine, diethanolamine, procaine, diethylamine, piperazine, tris (hydroxymethyl) aminomethane and tetramethylammonium hydroxide and so on. These salts can be prepared by standard methods, for example by reacting the free acid with an organic or inorganic base. In the presence of a basic group such as an amino group, acidic salts such as hydrochloride, hydrobromide, acetate, pamoate, etc. can be used as dosage forms; In the presence of an acidic group (such as —COOH)

or an alcohol group, medicinal esters such as acetate, maleate, pivaloyloxymethyl, etc., and esters known in the literature to improve solubility and hydrolysis can be used as sustained release and prodrug formulations.

BRIEF DESCRIPTION OF THE FIGURE

FIGS. 1A-1D are the result of the feeding experiment of mice in Example 1 of the present invention. Wherein, FIGS. 1A and 1B are the graphs showing the results of body weight of SPF mice fed with different sequences; FIGS. 1C and 1D are the graphs showing the results of fat weight in different parts of SPF mice with different feeding treatments. The data shown in the figure is the mean±standard deviation, the number of repetitions is 9-12, and the significant difference of each group is analyzed by Wilcoxon test, * representing a significance analysis result of P<0.05 and ** representing a significance analysis result of P<0.01.

FIGS. 2A and 2B are the feed intake monitoring graphs of SPF mice with different feeding treatments; FIGS. 2C and 2D are the graph showing the results of short-term feed intake measurement of SPF mice. The data shown in the figure is the mean±standard deviation, the number of repetitions is 9-12, and the significant difference of each group is analyzed by Wilcoxon test. * representing a significance analysis result of P<0.05,  representing a significance analysis result of P<0.01, * representing a significance analysis result of P<0.001.

FIG. 3 is a photograph of the body size of the SPF mice in Example 1 of the present invention after feeding with D3 for 8 weeks.

FIGS. 4A and 4B are graph showing the results of qPCR detection of the abundance of *A. muciniphila* in Example 1 of the present invention.

FIGS. 5A-5C are a graph showing the results of verification experiment of intestinal flora of GF mice in Example 1 of the present invention. FIG. 5A is the results of body weight of GF mice fed with D3; FIG. 5B is the results of fat weight in different parts of GF mice with different feeding treatments; FIG. 5C is the feed intake monitoring graphs of SPF mice with different feeding treatments. The data shown in the figure are the mean±standard deviation, the number of repetitions is 5-8, and the significant difference of each group is analyzed by Wilcoxon test, * representing a significance analysis result of P<0.05, ** representing a significance analysis result of P<0.01.

FIGS. 6A-6C are a graph showing the effect of D3 on the intestinal flora of mice in Example 1 of the present invention. Wherein, FIG. 6A is the graph showing the result of diversity analysis; FIG. 6B is the graph showing the result of PCOA analysis; FIG. 6C is the graph showing the result of LEfSc analysis, and shown in FIG. 2D is the graph showing the results of the qPCR detection of the abundance of *A. muciniphila*, in the figure, * representing a significance analysis result of P<0.05.

FIGS. 7A-7H are a graph showing the effect of using D3 on rats and rhesus monkeys in Example 2 of the present invention. FIG. 7A is the schematic diagram of sampling time point in rats; FIG. 7B is the graph showing the results of the growth rate of body weight with different feeding treatments of the rat; FIG. 7C is the graph showing the results of the short-term feed intake measurement of the rat; FIG. 7D is the graph showing the results of the qPCR detection of the abundance of *A. muciniphila* in intestine of rats with different feeding treatment; FIG. 7E is a schematic diagram of the sampling time point in rhesus monkeys; FIG. 7F is the graph showing the results of the growth rate of body weight with different feeding treatments of rhesus monkeys; FIG. 7G is the feed intake monitoring graphs of rhesus monkeys with different feeding treatments; FIG. 7H is the graph showing the results of the qPCR detection of the abundance of *A. muciniphila* in intestine of rhesus monkeys with different feeding treatment. The data shown in the figure are mean±standard deviation, the number of repetitions is 5-10, and the significant difference of each group is analyzed by Wilcoxon test. * representing a significance analysis result of P<0.05, ** representing a significance analysis result of P<0.01.

FIG. 8A is a volcano map of gene expression levels in the D3 vs HFD group; each circle represents a gene, and the diameter of the circle represents the value of FPKM, p<0.05 (light gray) and p<0.01 (black); FIG. 8B shows the relative expression level of Guca 2b gene in the ileum of SPF mice; FIG. 8C shows the relative level of Guca2b mRNA in the ileum of mice intragastrically administered with D3 or PBS; FIG. 8D shows the concentration of UGN in mice serum (ng/ml); FIG. 8E shows the results of immunofluorescent staining of ileal UGN. FIG. 8F is the UGN concentration (ng/ml) in the rat serum; FIG. 8G is the relative level of Guca2b mRNA in the ileum of rats intragastrically administered with D3 or PBS; FIG. 8H is the UGN concentration (ng/ml) in the macaque serum. The data shown in the figure are mean±standard deviation, the number of repetitions is 3-10, and the significant difference of each group is analyzed by Wilcoxon test. * representing a significance analysis result of P<0.05, ** representing a significance analysis result of P<0.01.

THE BEST WAY TO IMPLEMENT AN INVENTION

Figure 1A:
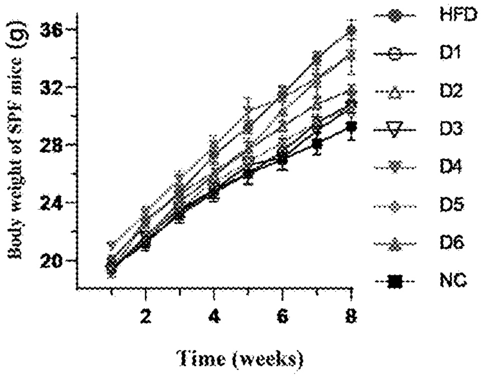

The present invention will be further described in detail below in conjunction with specific embodiments, and the given examples are only for clarifying the present invention, not for limiting the scope of the present invention. The examples provided below can be used as a guideline for those skilled in the art to make further improvements, and are not intended to limit the present invention in any way.

The experimental methods in the following examples are conventional methods unless otherwise specified. Materials, reagents, etc. used in the following examples, unless otherwise specified, are conventional biochemical reagents, which can be obtained from commercial sources.

1 Small Peptide

A series of highly hydrophobic 9-peptide, which can be collectively referred to as HD, are screened by the inventors with the following amino acid sequence formula (N-terminal to C-terminal):

HD: $X_1TX_2YX_3RTGR$ (SEQ ID NO. 9)

Wherein, the letter T represents threonine (Thr), the letter Y represents tyrosine (Tyr), the letter R represents arginine (Arg), and the letter G represents glycine (Gly); $X_1$ can be one of glycine (Gly, G) and arginine (Arg, R); $X_2$ can be one of arginine (Arg, R) and cysteine (Cys, C); $X_3$ can be one of lysine (Lys, K) and cysteine (Cys, C).

There are 8 kinds of 9-peptide that conform to the HD formula, and the specific amino acid sequence is as follows:

D1: RTRYKRTGR (as shown in SEQ ID NO: 1 in the sequence listing);

D2: GTCYKRTGR (as shown in SEQ ID NO: 2 in the sequence listing);

D3: RTRYCRTGR (as shown in SEQ ID NO: 3 in the sequence listing);

D5: RTCYKRTGR (as shown in SEQ ID NO: 4 in the sequence listing);

D7: GTCYCRTGR (as shown in SEQ ID NO: 5 in the sequence listing);

D8: GTRYKRTGR (as shown in SEQ ID NO: 6 in the sequence listing);

D9: RTCYCRTGR (as shown in SEQ ID NO: 7 in the sequence listing);

D10: GTRYCRTGR (as shown in SEQ ID NO: 8 in the sequence listing).

In addition, two similar 9-peptides that do not conform to the above formula are used as controls, and the specific amino acids are as follows:

D4: ATCYRRTGR (SEQ ID NO. 10)

D6: ATRYCRTGR (SEQ ID NO. 11)

All the polypeptides in the following examples are synthesized by the company, and the purity of the synthesized polypeptides is greater than 95%.

2 Experimental Animals

C57/B16J mouse is the standard strain, which is the product of SPF Biotechnology Co., Ltd. (Beijing, China).

Germ-free (GF) C57Bl/6 mice are products of the Department of Experimental Animal Science, Army Medical University, Chongqing, China.

Sprague Dawley (SD) rats are the standard strain, which is a product of SPF Biotechnology Co., Ltd. (Beijing, China).

Rhesus monkey is a standard strain and is a product of Beijing Zhongke Lingrui Biotechnology Co., Ltd.

3 Feed

#2150230401 standard feed is the product of Beijing Zhongke Lingrui Biotechnology Co., Ltd. The main components are: corn, soybean meal, flour, fish meal, oil, salt, calcium hydrogen phosphate, stone powder, multi-vitamins, multi-mineral elements, amino acids, etc. The feeding amount is 0.15 kg/day/only.

The high-fat diet (45 kcal % fat) is made by mixing the following raw materials: 300 g soybean meal, 250 g red-skinned eggs (equivalent to 55.5 g dry matter), 150 g cornmeal, 150 g wheat flour, 100 g whole milk powder, 100 g white sugar, 160 g lard, 3 g salt, 2.5 g calcium carbonate (or 8 g calcium gluconate), appropriate amount of yeast powder, and appropriate amount of baking powder. The total energy is 4646.4 kcal, the energy supplied by fat is 2107.8 kcal, the energy supplied by protein is 797.6 kcal, the energy supplied by carbohydrate is 1713.2 kcal, and the energy supplied by fat accounts for 45.3%.

All data in the following examples are analyzed for significance using Wilcoxon test.

Quantitative experiments in the following examples, unless otherwise specified, are set up to repeat the experiments three times, and the results are averaged.

Example 1 Mice Experiment

1. SPF Mice Experiments

C57/B16J mice were used in the SPF mice experiment. At the beginning of the experiment, C57/B16J mice were 4 weeks old, and each weighed 15±1 g. They were raised in a room with suitable temperature and humidity control, and the light/dark cycle was 12 hours, free diet and drinking water, and fed with standard laboratory feed (also known as growth and reproduction feed, item number SPFSLFZ003, product of SPF (Beijing) Experimental Animal Technology Co., Ltd.). After one week of adaptation, they were randomly assigned to a cage, 4-6 mice per cage.

1.1 SPF Mice Feeding Experiment

A total of 12 treatments were set up, each with 2 cages of C57/B16J mice, and each treatment was subjected to different feeding treatments, specifically as follows:

NC group (i.e. normal diet group): fed with standard laboratory feed (also known as growth and reproduction feed, SPFSLFZ003), free diet and drinking water, each intragastrically administrated with 0.2 ml solvent daily for 8 weeks.

HFD group (i.e. high-fat diet group): fed with high-fat diet, the high-fat diet used was rodent feed (containing 60% fat, D12492, formula reference Le Roy, T., et al. Dysosmobacter welbionis is a newly isolated human commensal bacterium preventing diet-induced obesity and metabolic disorders in mice. Gut (2021).), free diet and drinking water, each intragastrically administrated with 0.2 ml solvent daily for 8 weeks.

D1 group (i.e. high-fat diet+D1 intragastric administration group): fed with high-fat diet, free diet and drinking water. Intragastrically administrated with synthetic D1, 0.75 mg-3 mg/Kg body weight, 0.2 ml, once/day for 8 weeks.

D2 group (i.e. high-fat diet+D2 intragastric administration group): fed with high-fat diet, free diet and drinking water. Intragastrically administrated with synthetic D2, 0.75 mg-3 mg/Kg body weight, 0.2 ml, once/day for 8 weeks.

D3 group (i.e. high-fat diet+D3 intragastric administration group): fed with high-fat diet, free diet and drinking water. Intragastrically administrated with synthetic D3, 0.75 mg-3 mg/Kg body weight, 0.2 ml, once/day for 8 weeks.

D4 group (i.e. high-fat diet+D4 intragastric administration group): fed with high-fat diet, free diet and drinking water. Intragastrically administrated with synthetic D4, 0.75 mg-3 mg/Kg body weight, 0.2 ml, once/day for 8 weeks.

D5 group (i.e. high-fat diet+D5 intragastric administration group): fed with high-fat diet, free diet and drinking water. Intragastrically administrated with synthetic D5, 0.75 mg-3 mg/Kg body weight, 0.2 ml, once/day for 8 weeks.

D6 group (i.e. high-fat diet+D6 intragastric administration group): fed with high-fat diet, free diet and drinking water. Intragastrically administrated with synthetic D6, 0.75 mg-3 mg/Kg body weight, 0.2 ml, once/day for 8 weeks.

D7 group (i.e. high-fat diet+D7 intragastric administration group): fed with high-fat diet, free diet and drinking water. Intragastrically administrated with synthetic D7, 0.75 mg-3 mg/Kg body weight, 0.2 ml, once/day for 8 weeks.

D8 group (i.e. high-fat diet+D8 intragastric administration group): fed with high-fat diet, free diet and drinking water. Intragastrically administrated with synthetic D8, 0.75 mg-3 mg/Kg body weight, 0.2 ml, once/day for 8 weeks.

D9 group (i.e. high-fat diet+D9 intragastric administration group): fed with high-fat diet, free diet and drinking water. Intragastrically administrated with synthetic D9, 0.75 mg-3 mg/Kg body weight, 0.2 ml, once/day for 8 weeks.

D10 group (i.e. high-fat diet+D10 intragastric administration group): fed with high-fat diet, free diet and drinking water. Intragastrically administrated with synthetic D10, 0.75 mg-3 mg/Kg body weight, 0.2 ml, once/day for 8 weeks.

The feed intake was tracked every week. After the experiment, the mice were weighed and photographs were taken to compare the body size of the mice. After that, the mice were killed by cervical dislocation. The heart, liver, spleen, lung, kidney, blood, ileum, cecum, and colon were harvested, immediately placed in liquid nitrogen, and stored at −80° C. for further analysis. Precisely dissected and subcutaneous and visceral fat deposits were weighed.

Figure 1C:
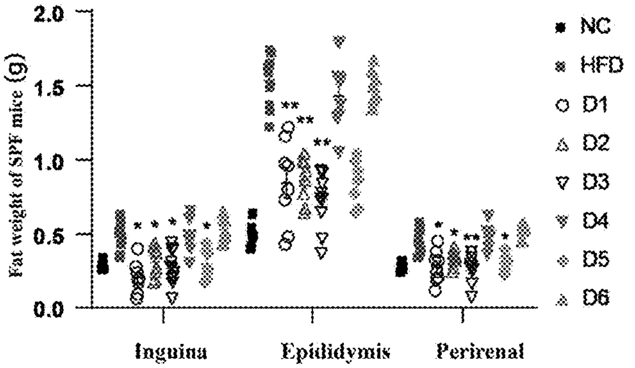
Figure 1B:
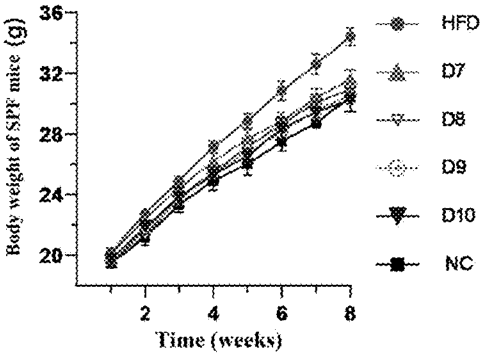
Figure 1D:
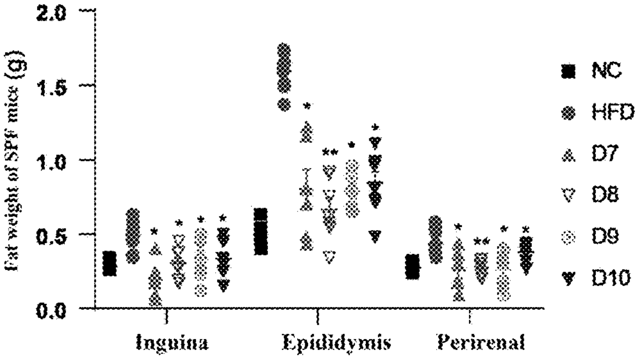

The body weight results of the mice were shown in figure a and figure b of FIG. 1: Compared with the HFD group, the body weight of the SPF mice decreased in all D1-D10 group after 8 weeks of treatment, and excepted for D4 (decreased by 3.55%) and D6 (decreased by 3.78%), all showed significant declines, specifically D1 group decreased by 11.62%, D2 group decreased by 9.45%, D3 group decreased by 12.06%, D5 group decreased by 11.8%, D7 group decreased by 8.08%, D8 group decreased 10.07%, D9 group decreased by 11.09%, D10 group decreased by 11.06%.

The body size of the mice was significantly different, and the body size of the mice treated with medicines, especially the D3 group for 8 weeks was smaller than that of the HFD group (see FIG. 3).

The results of weighing subcutaneous and visceral fat were shown in figure c and figure d of FIG. 1. It was found that no matter in the inguinal subcutaneous, epididymis or perirenal fat, the HD group (that is, D1 group, D2 group, D3 group, D5 group, D7 group, D8 group, D9 group, D10 group) were significantly lower than that of the HFD group, but slightly higher than that of the NC group.

Figure 2A:
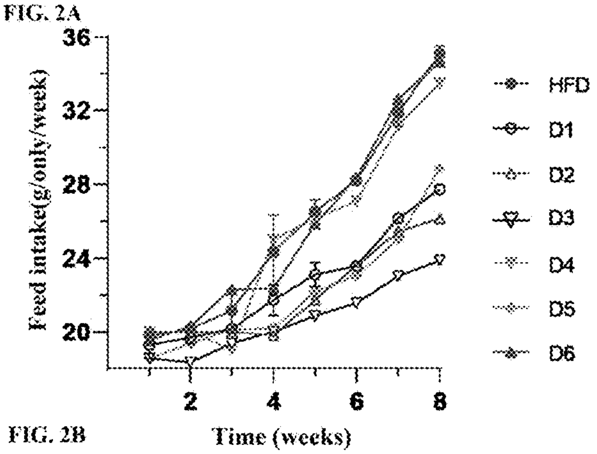
FIGS. 2A-2D are a graph showing the results of feed intake of SPF mice in Example 1 of the present invention.
Figure 2C:
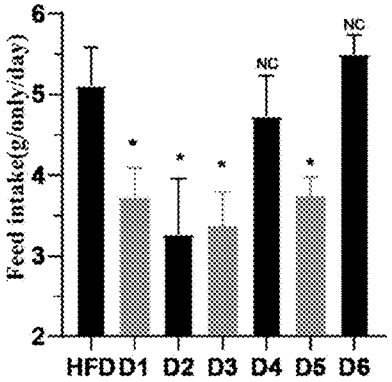
Figure 2B:
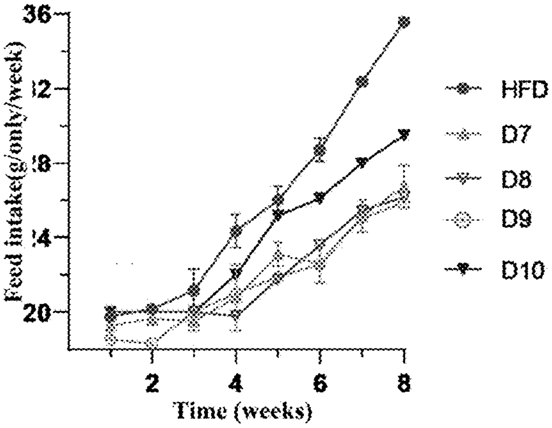
Figure 2D:
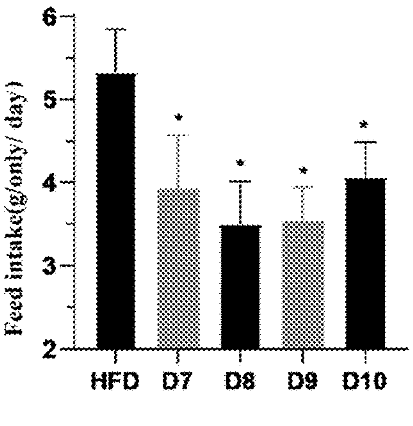

The results of weekly tracking and counting of feed intake were shown in figure a and figure b of FIG. 2. It was found that after 3-4 weeks, there was a significant difference in feed intake between the HD group and the control HFD group. The above showed that HD (D1, D2, D3, D5, D7, D8, D9 and D10) may play a role in inhibiting the formation of obesity by inhibiting the appetite of mice, especially D3 had a more significant effect, while D4 and D6 had no significant effect.

1.2 Short-Term Feed Intake Experiment of SPF Mice

A total of 2 treatments were set up, each with one cage of C57/B16J mice, and the high-fat diet used was rodent feed (containing 60 kcal % fat, D12492), and each treatment was subjected to different feeding treatments, specifically as follows:

HFD group (i.e. high-fat diet group): fed with high-fat diet.

D1 group (i.e. high-fat diet+D1 intragastric administration group): fed with high-fat diet, free diet and drinking water. Intragastrically administrated with synthetic D1, 0.75 mg-3 mg/Kg body weight, 0.2 ml, once/day for 8 weeks.

D2 group (i.e. high-fat diet+D2 intragastric administration group): fed with high-fat diet, free diet and drinking water. Intragastrically administrated with synthetic D2, 0.75 mg-3 mg/Kg body weight, 0.2 ml, once/day for 8 weeks.

D3 group (i.e. high-fat diet+D3 intragastric administration group): fed with high-fat diet, free diet and drinking water. Intragastrically administrated with synthetic D3, 0.75 mg-3 mg/Kg body weight, 0.2 ml, once/day for 8 weeks.

D4 group (i.e. high-fat diet+D4 intragastric administration group): fed with high-fat diet, free diet and drinking water. Intragastrically administrated with synthetic D4, 0.75 mg-3 mg/Kg body weight, 0.2 ml, once/day for 8 weeks.

D5 group (i.e. high-fat diet+D5 intragastric administration group): fed with high-fat diet, free diet and drinking water. Intragastrically administrated with synthetic D5, 0.75 mg-3 mg/Kg body weight, 0.2 ml, once/day for 8 weeks.

D6 group (i.e. high-fat diet+D6 intragastric administration group): fed with high-fat diet, free diet and drinking water. Intragastrically administrated with synthetic D6, 0.75 mg-3 mg/Kg body weight, 0.2 ml, once/day for 8 weeks.

D7 group (i.e. high-fat diet+D7 intragastric administration group): fed with high-fat diet, free diet and drinking water. Intragastrically administrated with synthetic D7, 0.75 mg-3 mg/Kg body weight, 0.2 ml, once/day for 8 weeks.

D8 group (i.e. high-fat diet+D8 intragastric administration group): fed with high-fat diet, free diet and drinking water. Intragastrically administrated with synthetic D8, 0.75 mg-3 mg/Kg body weight, 0.2 ml, once/day for 8 weeks.

D9 group (i.e. high-fat diet+D9 intragastric administration group): fed with high-fat diet, free diet and drinking water. Intragastrically administrated with synthetic D9, 0.75 mg-3 mg/Kg body weight, 0.2 ml, once/day for 8 weeks.

D10 group (i.e. high-fat diet+D10 intragastric administration group): fed with high-fat diet, free diet and drinking water. Intragastrically administrated with synthetic D10, 0.75 mg-3 mg/Kg body weight, 0.2 ml, once/day for 8 weeks.

According to the above treatment, it was carried out for 8 weeks, and then within 1 week, the mice were starved for one day and then given feed, and the feed intake of the animals in the following day was recorded. That is, food weights were recorded every other day (4 separate measurements) and the average daily intake was determined for each 2-day period and calculated for each individual during the one-week measurement period. The obtained were the results of the short-term intake statistics (unit: g/only/day).

The results were shown in figure c and figure d of FIG. 2, and it was verified that the HD group may inhibit the formation of obesity by inhibiting the appetite of mice, while D4 and D6 had no significant effect.

Based on the above results, it is speculated that the effect of D3 was more excellent, so the following experiments on germ-free mice, rats and macaques were all carried out with D3 as the treatment group.

2. GF Mice Experiment

To further determine the relative contribution of the microbiota to the anti-obesity effects of HD, D3 was chosen for GF mice experiment.

Germ-free (GF) C57Bl/6 mice were used in the GF mice experiment, kept in a germ-free isolator, and their GF status was verified by fecal PCR every month. At the beginning of the experiment, germ-free (GF) C57Bl/6 mice were 4 weeks old, each weighed 14±1 g. They were raised in a room with suitable temperature and humidity control, and the light/dark cycle was 12 hours, free diet and drinking water, and fed with standard laboratory feed (growth and reproduction feed, SPFSLFZ003, product of SPF (Beijing) Experimental Animal Technology Co., Ltd.), after one week of adaptation, they were randomly assigned to each cage, 4-6 mice per cage. A total of 3 treatments were set up, each with 1 cage, and each treatment was subjected to different feeding treatments, specifically as follows:

NC group (i.e. normal diet group): fed with standard laboratory feed (also known as growth and reproduction feed, SPFSLFZ003), free diet and drinking water for 8 weeks.

HFD group (i.e. high-fat diet group): fed with high-fat diet, the high-fat diet used was rodent feed (containing 60 kcal % fat, D12492), free diet and drinking water for 8 weeks.

D3 group (i.e. high-fat diet+D3 medicine intragastric administration group): fed with high-fat diet, free diet and drinking water. Intragastrically administrated with D3 medicine, 0.75 mg-3 mg/Kg body weight, 0.2 ml, once/day for 8 weeks.

Food intake and body weight were monitored weekly.

After the experiment on GF mice, the mice were killed by cervical dislocation. The heart, liver, spleen, lung, kidney, blood, ileum, cecum, and colon were harvested, immediately placed in liquid nitrogen, and stored at −80° C. for further analysis. Precisely dissected and subcutaneous and visceral fat deposits were weighed.

The body weight and fat results were shown in FIG. 5: Compared with the HFD group, the body weight of the mice treated with small peptide D3 for 8 weeks decreased significantly (figure a of FIG. 5). Subcutaneous and visceral fat were weighed, and it was found that no matter in the inguinal subcutaneous, epididymis or perinephric fat, the D3 group was significantly lower than that of the HFD group, but slightly higher than that of the NC group (figure b of FIG. 5). By tracking and counting the feed intake every week, it was found that after 3-4 weeks, the feed intake of the D3 group and the control HFD group gradually showed a significant gap (figure c of FIG. 5), which showed that D3 may inhibit the formation of obesity by inhibiting the appetite of mice, which was consistent with the experimental results of SPF mice.

At this time, in order to further confirm whether the reason for the weight loss of the SPF mice was related to the change of the ecological structure of the intestinal flora, the feces of mice in NC, HFD and D3 groups collected in the previous SPF mice experiment were analyzed by 16s amplicon sequencing. sequencing method (reference: Quan, L H, et al. Myristoleic acid produced by enterococci reduces obesity through brown adipose tissue activation. Gut 69, 1239-1247 (2020).) was used to analyze the fecal flora of mice. The analysis results of the fecal flora of SPF mice were shown in FIG. 6: diversity analysis (figure a of FIG. 6) and PCOA (figure b of FIG. 6) found that the fecal flora of mice treated with D3 was significantly different from that of the HFD group, and LEfSc analysis (figure c of FIG. 6) showed a significant increase in the abundance of *Bacteroides* and *A. muciniphila*, which were negatively associated with obesity in the D3 group, and conversely a significant decrease in the abundance of *Prevotella, Desulfovibrio* and Lawsonia, all of which have been shown to can promote the development of obesity. Also, the relative abundance of *A. muciniphila* in the intestinal flora of D3-treated mice was significantly increased ($p<0.05$) by qPCR.

3. Changes in the Abundance of *A. Muciniphila* in the Intestine of SPF Mice

In order to verify the changes in the relative abundance of *A. muciniphila* in the intestinal flora of mice fed with other HD, qPCR experiments were performed on the changes of intestinal flora in mice.

Faecal bacterial DNA was extracted from the faeces of mice in the NC, HFD, D1, D2, D3, D5, D7, D8, D9 and D10 groups collected in the pre-SPF mice experiments and then the relative abundance of *A. muciniphila* was determined using qPCR. The results were shown in FIG. 4 and indicated that the relative abundance of *A. muciniphila* in the intestinal flora of mice treated with HD (D1, D2, D3, D5, D7, D8, D9 and D10) was all significantly increased ($p<0.05$).

Example 2 Rat Experiment and Rhesus Monkey Experiment

1. Rat Experiment 1.1 Feeding Experiment

Sprague Dawley (SD) rats were used in the rat experiment. At the beginning of the experiment, the rats were 4 weeks old, and each weighed 137±5 g. They were raised in a room with suitable temperature and humidity control, and the light/dark cycle was 12 hours, free diet and drinking water, and fed with standard laboratory feed (a growth and reproduction feed, SPFSLFZ003). After one week of adaptation, they were randomly assigned to a cage. HD treatment was represented by D3, a total of 3 treatments were set up, and each treatment was subjected to different feeding treatments, specifically as follows (see figure a of FIG. 7):

NC group (i.e. normal diet group): 8 rats were fed with standard laboratory feed (also known as growth and reproduction feed, SPFSLFZ003), free diet and drinking water for 10 weeks.

HFD group (i.e. high-fat diet group): 8 rats were fed with high-fat diet, the high-fat diet used was rodent feed (containing 60 kcal % fat, D12492), free diet and drinking water for 10 weeks.

D3 group (i.e. high-fat diet+D3 medicine intragastric administration group): 10 rats were fed with high-fat diet, free diet and drinking water. Intragastrically administrated with HD (choose D3), 0.5 mg-2 mg/Kg body weight, 0.5 ml, once/day for 10 weeks.

Body weights were monitored weekly. Fresh excreta from these animals were collected and stored at −80° C. for further analysis by amplicon sequencing and the rats were euthanized at the end of the experiment.

The results were shown in FIG. 3: after 10 weeks of D3 treatment, the body weight of rats in the treatment group was significantly lower than that of the HFD group, and the growth rate of body weight decreased by 8.96±3.11% (figure b of FIG. 7). The relative abundance of *A. muciniphila* in the intestine of macaque after HD treatment was significantly increased ($p<0.05$) (figure d of FIG. 7)

1.2 Short-Term Feed Intake Experiment of SPF Rats

A total of 2 treatments were set up, with 5 rats in each treatment, and each treatment was subjected to different feeding treatments, specifically as follows: HFD group (i.e. high-fat diet group): 8 rats were fed with high-fat diet, the high-fat diet used was rodent feed (containing 60 kcal % fat, D12492), free diet and drinking water for 8 weeks.

D3 group (i.e. high-fat diet+D3 medicine intragastric administration group): 10 rats were fed with high-fat diet, free diet and drinking water. Intragastrically administrated with HD (choose D3), 0.5 mg-2 mg/Kg body weight, 0.5 ml, once/day for 8 weeks.

According to the above treatment, it was carried out for 8 weeks, and then within 1 week, the rats were starved for one day and then given feed, and the feed intake of the animals in the following day was recorded. That is, food weights were recorded every other day (4 separate measurements) and the average daily intake was determined for each 2-day period and calculated for each individual during the one-week measurement period. The obtained were the results of the short-term intake statistics (unit: g/only/day).

The results were shown in figure c of FIG. 7, indicating that the daily feed intake of rats in D3 group was significantly lower than that in HFD group ($p<0.05$).

2. Macaque Experiment

Rhesus monkeys were used in the macaque experiment. 9 in total, 18 weeks old at the beginning of the experiment, and each weighed 2.5±0.5 Kg. They were raised individually in the same environment, in a room with suitable temperature and humidity control, and the light/dark cycle was 12 hours, free diet and drinking water, and fed with standard laboratory feed (#2150230401). After 7 days of adaptation, they were randomly assigned to 3 groups with 3 animals in each group, and each group was subjected to different feeding treatments, specifically as follows (see figure e of FIG. 7):

NC group (i.e. normal diet group): fed with standard laboratory feed (#2150230401), free diet and drinking water for 6 weeks.

HFD group (i.e. high-fat diet group): fed with high-fat diet (45 kcal % fat), free diet and drinking water for 6 weeks.

D3 group (i.e. high-fat diet+D3 medicine intragastric administration group): fed with high-fat diet (45 kcal % fat), free diet and drinking water for 6 weeks. HD medicines were selected as D3, intragastrically administrated with D3, 0.5 mg-1 mg/Kg body weight, and intragastrically administrated according to 1.7 ml/K g body weight, once/day.

Food intake (unit: g/only/week) and body weight were monitored weekly. Fresh excreta of the above animals were collected and stored at −80° C. for further analysis of macaque fecal flora (method as above).

The results were shown in FIG. 7: after 6 weeks, the growth rate of body weight of the D3 treatment group decreased significantly (figure f of FIG. 7), while the results of feed intake were similar but not significant (figure g of FIG. 7). In addition, the relative abundance of *A. muciniphila* in the intestine of macaque after D3 treatment was significantly increased ($p<0.05$) (figure h of FIG. 7)

Example 3 Exploration of Molecular Mechanism of Action

1. Ileum Transcriptome Sequencing

In order to find the target genes that D3 may act on, the inventors performed ileal transcriptome analysis. Three samples from each group of mice were selected as targets for transcriptome sequencing. Ileal RNA was extracted using the Trizol method and an Agilent 2100 analyser was required to detect the RNA quality above 7 for RNA library construction. After passing the sample test, 2 g of total RNA was taken from each sample to construct a transcriptome sequencing library. After data acquisition, the RNA-seq data was first de-redundantly removed using Trim galore v0.4.4 to remove junctions and low quality sequences. Using GRCm38 as the mice reference genome, HISAT2 v2.0.5 and StringTie v1.3.4 were used to quantify the abundance of each gene. Differential expression analysis was performed using DESeq2 v1.24.0.

qPCR gene expression was carried out using the StepOnePlus real-time fluorescent quantitative PCR system. Three technical replicates were performed for each sample, and the identity and purity of the amplified product were checked by analyzing the melting curve at the end of the amplification. Gene expression results were referenced to the percent expression of each gene normalized to glyceraldehyde-3-phosphate dehydrogenase (GAPDH).

2. ELISA Detection of Serum UGN in Mice, Rats and Macaques

Serum preparation: mice were placed at room temperature for 2 hours or 4° C. overnight after eye vein blood collection, and centrifuged at 1000×g for 15 minutes at 2-8° C.; the supernatant can be taken for immediate detection; or sub-packaged, and the specimens were stored at −20° C. or −80° C., but repeated freezing and thawing should be avoided. Thawed samples should be centrifuged again prior to detecting.

The serum sample diluent was diluted 1:200 times and then tested. The specific operation was as follows: 5 μl of the sample was added to 45 μl of the sample diluent (1:10 dilution) and mixed. Then 15 μl of the above diluent was added to the 285 μl sample diluent (1:20 dilution) and mixed. The sample obtained after the completion of the second step was 1:200 times dilution. The sample incubation, primary antibody, horseradish peroxidase labeled avidin working solution, color development, termination and enzyme labeling detection were carried out in turn.

3. Mice Ileum Immunofluorescence

After the ileum was taken out, it was embedded with OCT and sliced by freezing microtome. Immunofluorescence brief steps: after the sections were washed with PBS for 3 times, 4% paraformaldehyde was added, fixed at room temperature for 10 min, and then washed with PBS for 3 times; 0.5% Triton X-100 was added, permeation at room temperature for 5 min, then washed with PBS 3 times; cell blocking solution was added and blocked at room temperature for 30 min; primary anti-UGN specific antibody (1:200) was added, 4° C. overnight and washed 3 times with PBST; the secondary antibody (1:500) was added, reacted at room temperature for 2 h, washed twice with PBST and washed once with PBS. The cells were stained with g/mL DAPI for additional 10 minutes at 37° C. Cleaned and sealed. Microscopic observation was recorded.

Figure 8A:
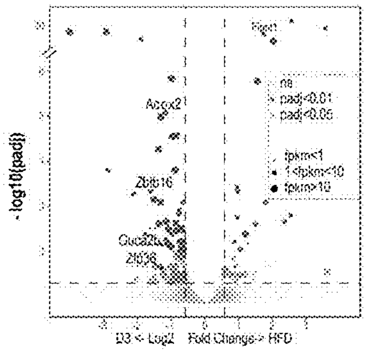
FIGS. 8A-8H are an effect diagram of the molecular action mechanism of D3 in Example 3 of the present invention.
Figure 8B:
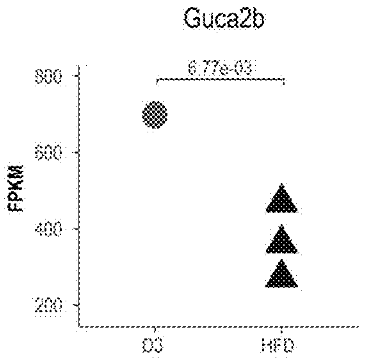
Figure 8C:
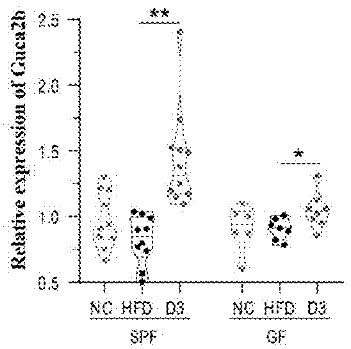
Figure 8D:
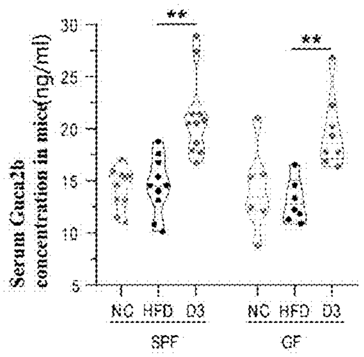
Figure 8E:
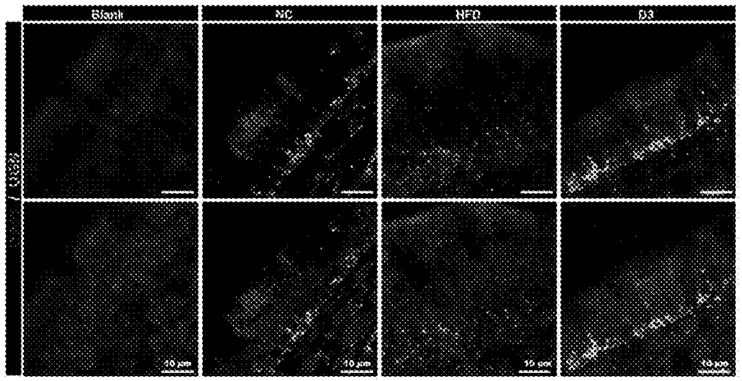
Figure 8F:
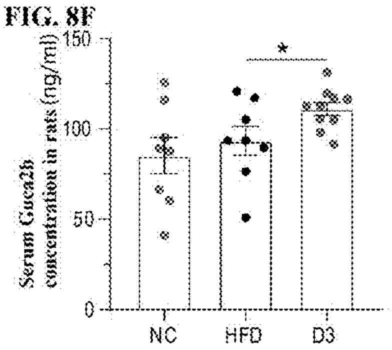
Figure 8G:
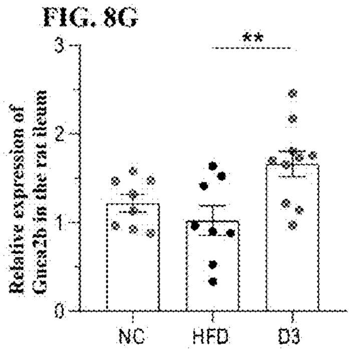
Figure 8H:
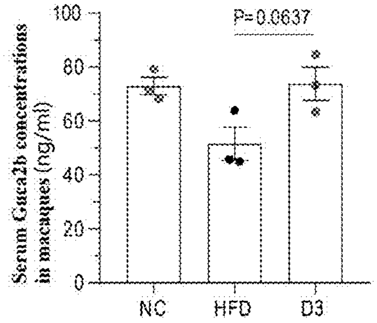

The results were shown in FIG. 8: DEseq was used to standardize the statistical number of genes in each sample, and the negative binomial distribution test was used to test the significance of the difference, and then the encoding genes of the differential proteins were obtained by combining the significance of the difference and the multiple of the difference. Firstly, the Top1000 genes were screened out according to P val less than or equal to 0.05, and the volcano map showed the differential analysis results, as shown in FIGS. 8A and B, the UGN encoding gene Guca2b (Padj<0.01) associated with the previously discovered phenotype of reduced feed intake became the inventor's main research object in the next step. The qPCR results of upper ileal genes in both SPF and GF mice verified the previous transcriptome results. It was undeniable that D3 significantly up-regulated the expression of UGN in SPF mice and GF mice ($P<0.01$) (FIG. 8*c*), and then the inventors further verified the changes of UGN levels in serum by ELISA (FIG. 8*d*). The inventors visualized the expression of UGN in mice ileal cells by immunofluorescence, as shown in FIG. 8*e*, the fluorescence intensity of UGN was significantly increased after D3 treatment.

The inventors then studied the changes of UGN content in serum of rats and macaques treated with D3 in the previous experiments in rats and macaques, and found that the level of Guca2b in rat serum was significantly increased ($P<0.05$), and the mRNA level of UGN in the ileum also increased significantly. Increased UGN levels were also found in the serum of macaque, but due to the small n value, the results were not significant (p=0.06). Past studies have demonstrated that Guca2b could regulate food intake through the UGN-GUCY2C gut-brain endocrine axis, thereby acting as a regulator of body weight homeostasis. This suggested that the effect of D3 on the appetite of mice may be effected by increasing the expression of UGN in the small intestine, increasing the level of UGN in the blood, and then acting on the GUCY2C receptor in the hypothalamus.

In summary, the 9-peptide HD can reduce the growth rate of body weight of experimental animals, and reduce the deposition of subcutaneous and visceral fat. In addition, it is speculated that the HD series of peptides could significantly inhibit the occurrence and development of dietary obesity in mice, rats and rhesus monkeys by reducing appetite, and that the abundance of the intestinal symbiotic bacterium *A. muciniphila* and serum UGN levels were significantly increased after HD treatment. The two peptides D4 and D6 that do not conform to this formula have no such effect.

The present invention has been described in detail above. For those skilled in the art, without departing from the spirit and scope of the present invention, and without unnecessary experiments, the present invention can be practiced in a wider range under equivalent parameters, concentrations and conditions. While specific embodiments of the present invention have been shown, it should be understood that the present invention can be further modified. In a word, according to the principles of the present invention, the present application intends to include any changes, uses or improvements to the present invention, including changes made by using conventional techniques known in the art and departing from the disclosed scope of the present application. Applications of some of the essential features are possible within the scope of the appended claims below.

INDUSTRIAL APPLICATIONS

The present invention discloses a polypeptide for inhibiting dietary obesity. The amino acid sequence thereof is as follows: $X_1TX_2YX_3$ RTGR (SEQ ID NO. 9). The present invention also provides the use of the polypeptide. The polypeptide of the present invention reduces the growth rate of body weight of experimental animals, reduces subcutaneous and visceral fat deposition, and can significantly inhibit the occurrence and development of dietary obesity in experimental animals such as mice, rats and rhesus monkeys by reducing appetite.

```
                      SEQUENCE LISTING

Sequence total quantity: 11
SEQ ID NO: 1           moltype = AA  length = 9
FEATURE                Location/Qualifiers
source                 1..9
                       mol_type = protein
                       organism = synthetic construct
SEQUENCE: 1
RTRYKRTGR                                                         9

SEQ ID NO: 2           moltype = AA  length = 9
FEATURE                Location/Qualifiers
source                 1..9
                       mol_type = protein
                       organism = synthetic construct
SEQUENCE: 2
GTCYKRTGR                                                         9

SEQ ID NO: 3           moltype = AA  length = 9
FEATURE                Location/Qualifiers
source                 1..9
                       mol_type = protein
                       organism = synthetic construct
SEQUENCE: 3
RTRYCRTGR                                                         9

SEQ ID NO: 4           moltype = AA  length = 9
FEATURE                Location/Qualifiers
source                 1..9
                       mol_type = protein
                       organism = synthetic construct
SEQUENCE: 4
RTCYKRTGR                                                         9

SEQ ID NO: 5           moltype = AA  length = 9
FEATURE                Location/Qualifiers
source                 1..9
                       mol_type = protein
                       organism = synthetic construct
SEQUENCE: 5
GTCYCRTGR                                                         9

SEQ ID NO: 6           moltype = AA  length = 9
FEATURE                Location/Qualifiers
source                 1..9
                       mol_type = protein
                       organism = synthetic construct
SEQUENCE: 6
GTRYKRTGR                                                         9
```

```
SEQ ID NO: 7            moltype = AA  length = 9
FEATURE                 Location/Qualifiers
source                  1..9
                        mol_type = protein
                        organism = synthetic construct
SEQUENCE: 7
RTCYCRTGR                                                          9

SEQ ID NO: 8            moltype = AA  length = 9
FEATURE                 Location/Qualifiers
source                  1..9
                        mol_type = protein
                        organism = synthetic construct
SEQUENCE: 8
GTRYCRTGR                                                          9

SEQ ID NO: 9            moltype = AA  length = 9
FEATURE                 Location/Qualifiers
source                  1..9
                        mol_type = protein
                        organism = synthetic construct
VARIANT                 1
                        note = X is glycine or arginine
VARIANT                 3
                        note = X is arginine or cysteine
VARIANT                 5
                        note = X is lysine or cysteine
SEQUENCE: 9
XTXYXRTGR                                                          9

SEQ ID NO: 10           moltype = AA  length = 9
FEATURE                 Location/Qualifiers
source                  1..9
                        mol_type = protein
                        organism = synthetic construct
SEQUENCE: 10
ATCYRRTGR                                                          9

SEQ ID NO: 11           moltype = AA  length = 9
FEATURE                 Location/Qualifiers
source                  1..9
                        mol_type = protein
                        organism = synthetic construct
SEQUENCE: 11
ATRYCRTGR                                                          9
```

The invention claimed is:

1. A polypeptide consisting of a sequence selected from the group consisting of SEQ ID NOs: 1-4, 6, and 8-9.

2. A pharmaceutical formulation comprising (i) a polypeptide consisting of a sequence selected from the group consisting of SEQ ID NOs: 1-4, 6, and 8-9, and (ii) a pharmaceutically acceptable excipient.

3. A polynucleotide sequence encoding a polypeptide sequence selected from the group consisting of SEQ ID NOs: 1-4, 6, and 8-9.

* * * * *